United States Patent
Buijtels

(10) Patent No.: US 6,385,507 B1
(45) Date of Patent: May 7, 2002

(54) ILLUMINATION MODULE

(75) Inventor: Antonius Gerardus Johannes Wilhelmina Maria Buijtels, Eindhoven (NL)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/763,403

(22) PCT Filed: Jun. 22, 2000

(86) PCT No.: PCT/EP00/05770

§ 371 Date: Feb. 22, 2001

§ 102(e) Date: Feb. 22, 2001

(87) PCT Pub. No.: WO01/01118

PCT Pub. Date: Jan. 4, 2001

(30) Foreign Application Priority Data

Jun. 24, 1999 (EP) .............................. 99202036

(51) Int. Cl.[7] .............................................. G06F 19/00
(52) U.S. Cl. .................... 700/245; 700/166; 700/167; 356/237.1; 356/243.1; 219/267; 219/269; 250/231.8; 250/231.14
(58) Field of Search ................................ 700/245, 275, 700/254, 258, 166, 167; 356/237.1, 632, 243.1; 382/150; 219/267, 269; 250/231.14, 231.8

(56) References Cited

U.S. PATENT DOCUMENTS

| 4,893,223 A | | 1/1990 | Arnold ........................ 362/252 |
| 5,058,178 A | * | 10/1991 | Ray ............................ 382/150 |
| 5,093,554 A | * | 3/1992 | Von Gaisberg et al. ..... 219/267 |
| 5,519,809 A | * | 5/1996 | Husseiny et al. ........... 704/275 |
| 5,569,912 A | * | 10/1996 | Turk et al. ............. 250/231.14 |
| 6,043,877 A | | 3/2000 | Land .......................... 356/243 |
| 6,122,042 A | * | 9/2000 | Wunderman et al. ......... 356/73 |
| 6,167,715 B1 | * | 12/2000 | Albeck et al. .............. 356/154 |
| 6,256,091 B1 | * | 7/2001 | Kobayashi ................. 382/23.1 |
| 2001/0016063 A1 | * | 8/2001 | Albeck et al. .............. 356/154 |

FOREIGN PATENT DOCUMENTS

EP   WO 01/01118 A1  *  6/2001

* cited by examiner

Primary Examiner—William A. Cuchlinski, Jr.
Assistant Examiner—McDieunel Marc
(74) Attorney, Agent, or Firm—Steven R. Biren

(57) ABSTRACT

An illumination module (20) for illuminating an object (10) comprises a number of illumination rings (62, 64, 66) each comprising a number of radiation-generating elements (50) which are all arranged on a flat plate (42). For each ring, a light guide (72, 82, 84) is provided for guiding the radiation from the ring to the exit window (60) where the radiation exits at a range of angles which are specific to said ring. The rings can be switched on individually, so that different kinds of illumination can be realized.

23 Claims, 5 Drawing Sheets

ILLUMINATION MODULE

BACKGROUND OF THE INVENTION

The invention relates to an illumination module for illuminating an object to be examined, which module comprises an exit window for radiation generated in the module, a module axis which extends perpendicularly to the central part of the exit window, and a number of radiation-generating elements which are arranged in at least two illumination rings, which illumination rings have a midpoint, which is situated on the module axis, and are individually switchable, the radiations of the different illumination rings passing through the exit window at different angles with respect to the module axis.

The invention also relates to an optical device for the observation of an object, which device is provided with such an illumination module, and to an apparatus for placing electronic components on a support, which apparatus is provided with at least one such optical device.

At present, said apparatus is often used to automatically, very accurately and very rapidly place electronic components on a support, such as a printed circuit board (PCB). Said apparatus comprises one or more robots, provided with a suction pipette, and an equally large number of placement stations associated with the relevant robots. The suction pipette receives a component to be placed from a component input device, whereafter the associated robot transports the suction pipette and the component to a position on a support which, at that instant, is situated in the placement station. Before the component can be placed on the support, it has to be identified and inspected for irregularities, and it must be checked whether the component is correctly oriented with respect to, for example, a system of coordinates of the robot. To this end, the placement station is provided with an optical observation device for observing the component held by the suction pipette, which observation device is alternatively referred to as vision module. This device comprises a camera by means of which an image of the component is converted into electric signals which are electronically processed. A good observation device should meet the following requirements: the image must be free of distortion, the observation device should also be capable of imaging large components, the aperture angle of the beam with which the component is illuminated must be relatively small, and, for specific applications, the angle of incidence of the illumination beam on the component must be as large as possible. To properly observe the component, it is necessary for this component to be illuminated in the right way. To achieve this, the observation device comprises an illumination module.

Such an illumination module is described in U.S. Pat. No. 4,893,223. The known illumination module comprises a large number of light-emitting diodes, also referred to as LEDs, which are mounted on the inner surface of a concave plate and arranged in rings or angle sectors. Since the components to be placed by means of the placement machine may demonstrate different shapes and different surface conditions, the illumination module should preferably be programmable, i.e. it should be possible for groups of LEDs, such as the LEDs of a ring or the LEDs of a corner sector, to be switched on individually, so that the angle at which the object is illuminated and/or the part of the object that is illuminated can be adjusted. The illumination module described in U.S. Pat. No. 4,893,223 is used to illuminate the free end, which is provided with a solder ball, of the connection pins of a component, which is commonly referred to as surface mounted device (SMD). The observation device wherein this illumination module is employed, makes it possible to inspect only the end of one pin of the SMD. To inspect a subsequent pin, the observation device and the SMD are moved with respect to each other. Thus, the illumination module described in U.S. Pat. No. 4,893,223 has a small illumination field, and the angle between the beam of the LEDs and the normal to the surface of the SMD is relatively small. The beams supplied by the LEDs have a relatively small aperture angle, of the order of 10°. The illumination module in accordance with U.S. Pat. No. 4,893,223 is difficult to manufacture because all LEDs must be accurately aligned to make sure that they all illuminate the same small area.

BRIEF SUMMARY OF THE INVENTION

It is an object of the invention to provide a programmable illumination module having a wide range of applications, which can be readily manufactured and has minimal dimensions, and which, in addition, can be adjusted for a large illumination field, and which is capable of supplying a very oblique illumination beam. This illumination module is characterized in that all the radiation-generating elements are provided on a flat plate which extends parallel to the central part of the exit window, and the principal rays of all radiation beams emitted by the radiation-generating elements extend parallel to the module axis.

The fact that this module is capable of supplying a very oblique illumination beam means that selected radiation, originating, for example, from the outermost illumination ring, includes a very small angle, of for example at least 6°, with the illuminated surface of the object.

The provision, with great accuracy, of the radiation-generating elements on a flat plate is simpler than the provision, with the same accuracy, of said elements on a concave plate. The flat plate may be embodied so as to be a printed circuit board with electric conductors via which the radiation-generating elements are fed.

A preferred embodiment of the illumination module is further characterized in that opposite each illumination ring there is provided a radiation guide which, in a plane at right angles to the module axis, is ring-shaped in section, the entrance plane of said radiation guide being situated opposite the associated illumination ring, and the shape of the light guide is exit plane situated opposite the entrance plane being adapted to the desired direction of the radiation to be supplied by the associated illumination ring.

The use of these radiation guides enables the optimum illumination direction for a specific application to be achieved. The radiation guide associated with a certain illumination ring also makes sure that the radiation from said ring is not mixed with radiation from other illumination rings. Since the radiation from an illumination ring is confined to the associated radiation guide until it exits via the exit plane of this guide, the beams of the radiation-generating elements can have a relatively large aperture angle, for example in the range from 20° to 30°. In addition, the radiation guide ensures, via total internal reflections, that the radiation beam leaving the radiation guide demonstrates a certain degree of homogeneity. In this regard, the length of the radiation guide and the aperture angle of the LEDs of the associated illumination ring play a part.

To further increase the homogeneity, the illumination module is preferably further characterized in that the exit surface of all radiation guides, with the exception of the outermost radiation guide, is provided with a diffuse body the surface of which facing away from the radiation guides has such a shape that the radiation beam exiting from a radiation guide through this surface has a desired direction.

The radiation guides may be filled with air. Preferably, however, the illumination module is characterized in that the radiation guides, possibly with the exception of the innermost radiation guide, are filled with a transparent synthetic resin.

In accordance with a further characteristic, the synthetic resin is polycarbonate or polymethyl methacrylate. These synthetic resins, which are also known by the abbreviations PC and PMMA, respectively, are highly transparent and of good optical quality.

Preferably, the illumination module is characterized in that scattering particles are integrated in the synthetic resins.

If so, these synthetic resins have a diffuse effect, and the relevant radiation guides can contribute to rendering the radiation leaving the illumination module uniform. The different radiation guides may exhibit different degrees of diffusion.

Under certain conditions it may be attractive to also fill the innermost radiation guide with a synthetic resin.

In accordance with a further characteristic of the illumination module, the outermost radiation guide has a reflective surface for reflecting radiation towards the exit plane of this radiation guide, which reflective surface consists of two parts which enclose an obtuse angle with each other.

Said reflective surface divides the radiation beam, which propagates through the radiation guide and which has a certain intensity distribution, into two sub-beams which are positioned at the location of the object such that the original intensity distribution is lost and a more uniform distribution is obtained. In this manner, also the radiation beam supplied by the outermost radiation guide obtains a sufficiently uniform distribution.

An embodiment of the illumination module which is attractive for the observation device of a component placement machine is characterized in that it comprises three illumination rings.

This illumination module is still compact enough to be fitted in the placement machine, and it also enables good illumination, with sufficient intensity and at different angles, of the components to be achieved.

For the radiation-generating elements use can be made of different elements. For example, use can be made of diode lasers. Diode lasers emit a relatively narrow beam of high intensity and the radiation thereof can be readily oriented in the desired direction. For the radiation-generating elements use can also be made of luminescing diodes, provided the elements do not have to be switched rapidly. A preferred embodiment of the illumination module is however characterized in that the radiation-generating elements are formed by LEDs.

These LEDs are inexpensive and available in different versions as regards radiation intensity, dimension and aperture angle.

Dependent upon the application of the illumination module, one or more illumination rings may comprise diode lasers and the other illumination rings may comprise LEDs. It is alternatively possible that one and the same illumination ring comprises a number of diode lasers as well as a number of LEDs.

The illumination module is preferably further characterized in that at least one of the illumination rings comprises at least two types of LEDs, which emit radiation of different wavelengths, and LEDs of the first type alternating with LEDs of the second type in said illumination ring.

For example, all illumination rings may comprise alternately red, green and blue LEDs which can be switched on in different combinations. As a result, the color of the illumination can be optimally adapted to the color of the object to be examined and/or the background thereof. The contrast of the observation device can thus be improved considerably, also if the camera of the observation device is a monochrome camera. It is alternatively possible to use LEDs of only two different colors, or provide LEDs of different colors in only one illumination ring, or provide only one type of LED in one and the same illumination ring; however, the LEDs of the different illumination rings are of a different kind.

An illumination module which is particularly suited for use in a component placement machine may further be characterized in that, within the central illumination ring, a transparent plate is provided which encloses an acute angle with the module axis.

By means of this plate, it can be precluded that a component which has fallen from the suction pipette situated above the illumination module can fall on the camera situated below the module.

This illumination module may be further characterized in that an optical filter is provided on the plate.

As a result, this plate may fulfill a second function. The filter may be a color filter by means of which it is precluded that ambient radiation, i.e. radiation not originating from the illumination module, can reach the camera. The filter may also be a grey filter by means of which the intensity of the illumination radiation originating from the component can be adapted to the sensitivity of the camera. This enables the illumination module to be used in combination with different cameras, or to further increase the intensity of the illumination radiation to a level above that of the ambient light so as to reduce the influence of the ambient light on the observation.

Another embodiment of the illumination module is characterized in that, within the central illumination ring, a semi-transparent plate is provided at an angle of, in principle, 45° with respect to the module axis, and in that an additional radiation source is provided which is arranged such that radiation from this source is incident on the semi-transparent plate and reflected thereby towards the exit window of the illumination module.

As the rays of the additional radiation source enclose angles in the range from 0° to, for example 20° with the module axis, the module can now provide a bright-field illumination for the object in addition to the dark-field illumination which is supplied by the radiation-generating elements of the illumination rings. In the case of a bright-field, or normal, illumination, radiation which is specularly reflected by the object is captured by the imaging optics and the camera, and the object is imaged as a bright object. Details of the object which scatter the illumination radiation, or reflect it outside the imaging optics, can now be observed against a bright background. In the case of a dark field, or oblique, illumination, the object reflects the illumination radiation outside the imaging optics. The scattering details of the object reflect the radiation in the imaging optics and the camera and are brightly imaged against a dark background.

The last-mentioned embodiment is preferably further characterized in that the additional radiation source is formed by a number of additional radiation-generating elements arranged along at least one row, in combination with a radiation-conducting plate the entrance face of which is directed towards the additional radiation-generating elements, and the exit face of which is directed towards the semi-transparent plate.

Preferably, the additional radiation-generating elements are arranged in at least one circle segment at one side of the semi-transparent plate.

In this case, the bright radiation field is shaped so as to be in the form of a ring segment the length of which is determined by the position of the midpoint of the semi-circle with respect to the center of the transparent plate.

In order to obtain a more two-dimensional foreground illumination, the illumination module is preferably further characterized in that a second radiation-guiding plate is arranged against the exit face of the first radiation-guiding plate at an angle of, in principle, 90° with respect to the first radiation-guiding plate, and in that a reflecting roof prism is situated at the location of the transition from the first radiation-guiding plate to the second radiation-guiding plate, so as to reflect, in two opposite directions in said plate, two halves of radiation exiting from the first radiation-guiding plate.

As said radiation halves are subject to total internal reflection in the second radiation guide, the beam incident on the semi-transparent plate is elongated in a direction transverse to the direction of the row of additional radiation-generating elements, and this beam additionally demonstrates a more uniform intensity distribution. The roof prism is embodied in such a manner, i.e. the angles thereof are chosen to be such that a part of the radiation leaving the first radiation guide is passed by the prism, so that radiation also exits through that, central, part of the exit plane of the second radiation-guiding plate, which is situated at the level of the roof prism.

In accordance with a further characteristic of this illumination module, the roof prism is provided in the second radiation-guiding plate.

Preferably, however, the illumination module is alternatively characterized in that the roof prism forms part of the first radiation-guiding plate.

If so, the prism can be more readily provided and, in addition, the optical properties of the second radiation-guiding plate are not adversely affected.

Preferably, this illumination module is further characterized in that the second radiation-guiding plate takes the form of a cylinder segment whose cylinder axis extends parallel to the module axis.

The outer ray of the second radiation-guiding plate can then be chosen to be such that the upper part of this plate can be slid into the innermost illumination ring, so that, also if the additional radiation-generating elements for the bright-field illumination are employed, the illumination module can remain compact.

The additional, radiation-generating elements can alternatively be formed by at least two kinds of elements which emit radiation of different wavelengths, whereby, in a row, elements of the first kind alternate with elements of the other kind(s). In this case, also the color of the bright-field illumination can be adjusted, which may yield a higher contrast.

The invention also relates to an observation device for observing an object, which observation device is provided with an illumination system for illuminating the object, and with a camera for receiving an image of the object. The observation device in accordance with the invention is characterized in that the illumination system is an illumination module as described hereinabove.

Finally, the invention also relates to a component-placement machine for placing electronic components on a support, which machine is provided with:

a frame;

at least one robot;

a transport system for transporting supports;

a placement head for each robot for placing components on a support, which placement head is secured to an arm of the robot, and component-positioning means for each robot for positioning a component which is held by the placement head associated with the robot.

This placement machine is characterized in that the observation device is a device as described hereinabove.

BRIEF DESCRIPTION OF THE SEVERAL VIEWS OF THE DRAWING(S)

These and other aspects of the invention will be apparent from and elucidated with reference to the embodiments described hereinafter.

DESCRIPTION OF THE PREFERRED EMBODIMENT

Figure 1:
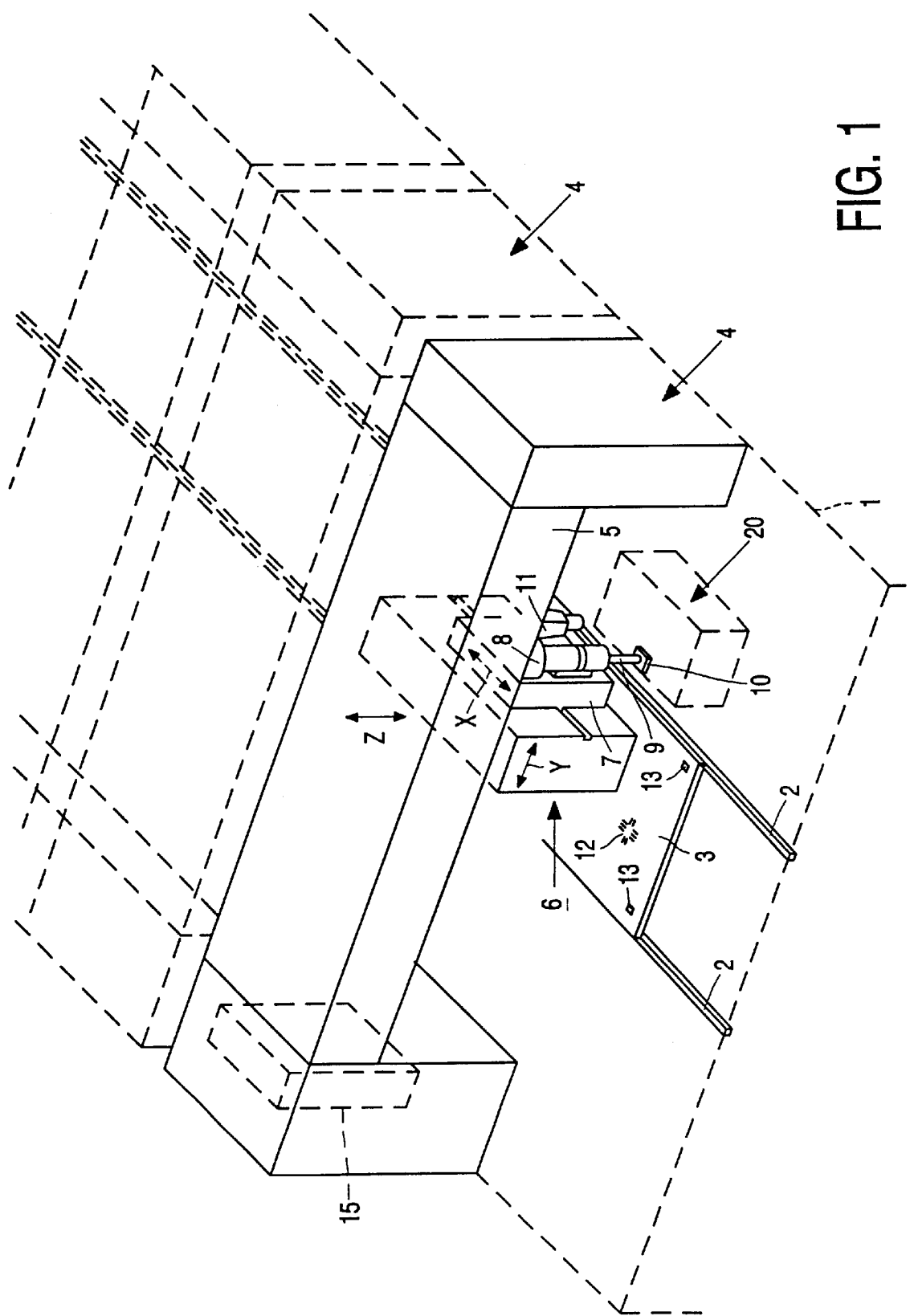
FIG. 1 shows an embodiment of a component placement machine.

FIG. 1 is a perspective view of an embodiment of a part of a component placement machine wherein the invention can be applied. Reference numeral 1 refers to the frame of the machine, which is indicated only diagrammatically by means of an interrupted line. On the frame there is a transport system, only the transport rails 2 of which are shown, for transporting carriers or printed circuit boards 3. Above the transport rails there is a component placement unit 4, which is formed by a U-shaped frame 5 to which an X-Y-Z robot 6 is secured. The X, Y and Z movements of the robot are indicated by means of arrows. The movement of the robot may alternatively be a $\Phi_r$ movement. A placement head 8, with which components can be placed on the carrier, is secured to an arm 7 of the robot.

The components to be placed are supplied by one or more belts on which the components are provided so as to be readily removable. These belts are transported by an equally large number of roller-feed systems, which systems also remove the components from the belts. Per placement unit, for example, five roller-feed systems may be present. Instead of roller-feed systems, use may alternatively be made of bulk-feed systems to supply the components. The component-supply system does not form part of the invention and, hence, is not shown in FIG. 1. Such a system is more elaborately described in PCT patent application WO 98/24291 (PHN 16111).

The placement head 8 is provided with a suction pipette 9 with which a component can be picked up and placed on a carrier 3. Also a video recording device 11 for the carrier is secured onto the arm 7. To accurately place a component on a carrier, the exact position of the location 12 where said component is to be placed on the carrier must be known. This position can be determined by recording certain identifying marks (fiducials) 13 on the carrier by means of the video-recording device, for example a camera. The relative position, with respect to such fiducials, of the location where the component must be placed on the carrier is known beforehand. The data on the position of these fiducials supplied by the video recording device 11 are supplied, in the form of an electric signal, to a signal processing unit 15 where they are compared to reference data stored in the unit 15, so that any deviations can be calculated.

Figure 2:
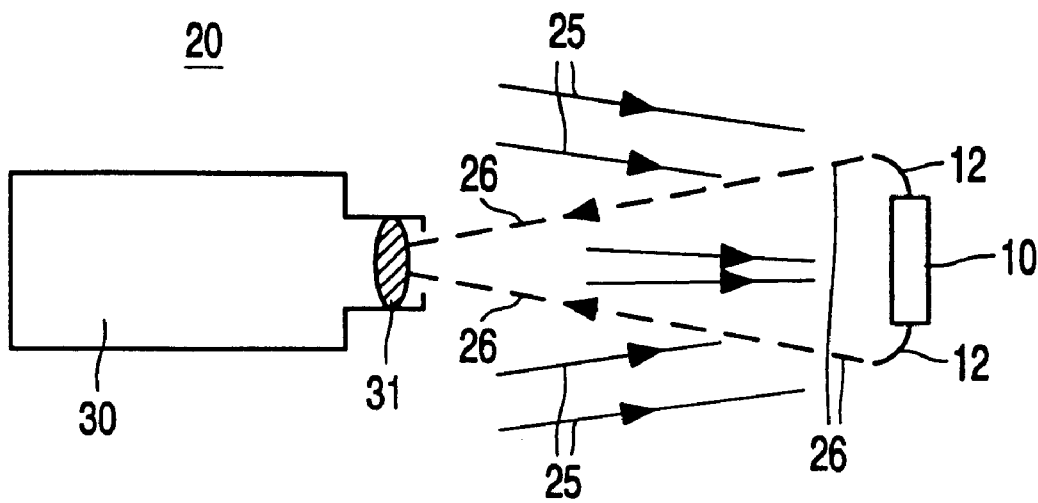
FIG. 2 shows the principle of the bright-field illumination.

The placement unit 4 is further provided with an optical observation device, indicated by block 20 in FIG. 1. This device can be used to determine the relative position of a component 10, or parts thereof such as the connection pins, with respect to the suction pipette. The observation device can also be used to identify or check a component 10, for example with respect to shape and quality. For this purpose, the suction pipette with the component 10 is moved in a position above the optical observation device. As shown in FIG. 2 and subsequent Figures, the observation device comprises an illumination module for illuminating the component and a video recording device, for example a CCD camera, for observing the component and generating an electric signal wherein data about the component, such as positional data, are contained. This signal is supplied to the signal processing unit 15 and compared to the data about the component stored in this unit. By means of the result of this comparison and the data about the position in which, for example, the connection pins must be placed, the robot 6 with the placement head can be controlled such that the component is placed at the desired location on the carrier, whereafter it can be secured onto the carrier.

As indicated in FIG. 1 by means of interrupted lines, the placement machine may alternatively be provided with a number of placement units 4 for simultaneously placing components on a number of carriers. Each placement unit is provided with a X-Y-Z robot, a placement head, a video recording device and a signal processing unit.

To obtain an accurate and reliable image of a component to be observed, the observation device or vision module must meet high requirements. Apart from a good camera and imaging optics, also good illumination of the component is of essential importance. A general requirement to be met is that the image of the component observed by the camera exhibits a homogeneous intensity and, for example, is not smaller at the edge than in the center. If this requirement is met, for example, image processing by means of the data supplied by the camera can be kept relatively simple. Particularly in an observation device of a placement machine which should be capable of placing different types of components, such as SMD components, Ball Grid Arrays (BGAs) or smooth, reflective components, different illumination possibilities should be available. In order to be properly observable, each type of component requires a different illumination. In addition, it should be possible to properly observe a specific detail of the component, which also requires specific illumination highlighting the relevant detail.

In the illumination technique used in the observation devices described herein, a distinction is made between bright-field illumination and dark-field illumination. In the case of bright-field illumination, a radiation beam with an aperture angle of, for example, maximally 20° is used, the principal ray being sent, in principle, at right angles to the object, or a specific detail thereof, and the camera detects the radiation reflected by the object or the detail, which radiation is captured by the imaging optics and the camera. The surroundings of the object, or the detail, are not observed by the camera and appear to be black. FIG. 2 shows the principle of bright-field illumination. This Figure shows a component 10 with connection pins 12, and a camera 30 with an objective lens 31. The illumination radiation is indicated by means of radiation arrows 25. The camera only captures the radiation reflected by the component which is situated within the border rays 26 indicated by means of interrupted lines. This type of illumination enables an object to be observed as bright against a dark background. This illumination can also be used to observe details of the object if these details are in contrast with the rest of the object because they have a different reflection coefficient and hence appear brighter or darker than the rest of the object, or because they scatter radiation and hence appear darker than the rest of the object.

Figure 3:
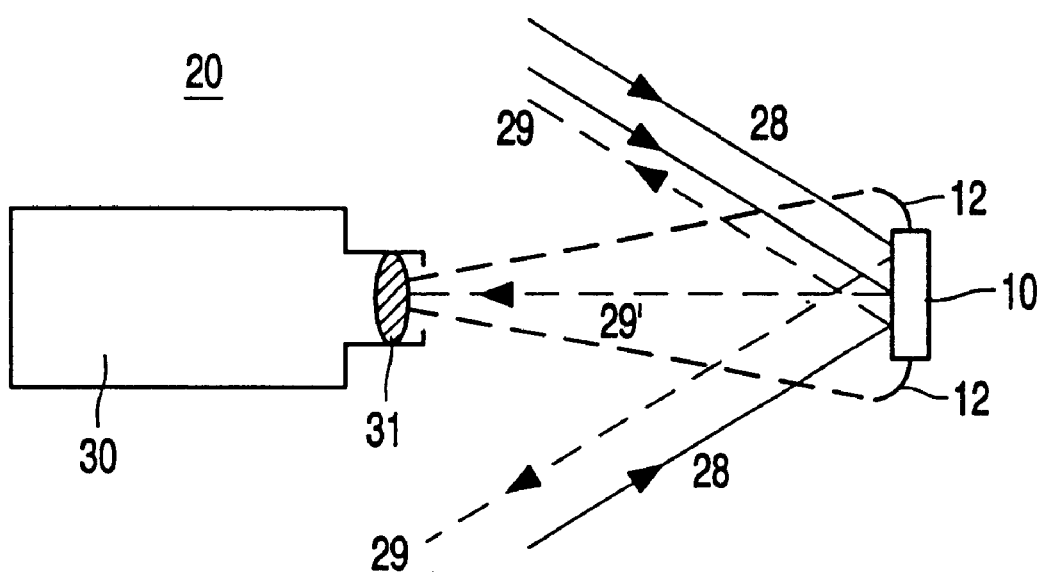
FIG. 3 shows the principle of the dark-field illumination.

FIG. 3 shows the principle of dark-field illumination. The illumination radiation, indicated by means of arrows 28, is incident on the object or component 10, 12 at such angles of incidence, for example 40° to 70°, that the reflective radiation, indicated by means of broken rays 29, does not pass through the imaging optics 31 and the camera 30, so that the object itself is not observed by the camera. A scattering detail 32 of the object, however, may deflect part of the radiation at such an angle that this part can pass through the imaging optics. This detail is observed as bright against a dark background. Using this type of illumination, for example, also the contours of an object can be properly observed. If certain details of a component must be highlighted, use is preferably made of so-called grazing illumination, i.e. illumination whose rays enclose angles of, for example, 70° to 88° with the normal to the component. Since this radiation is reflected more strongly outside the imaging optics, and only the radiation reflected by scattering details can reach the camera, only these details are observed.

Figure 4:
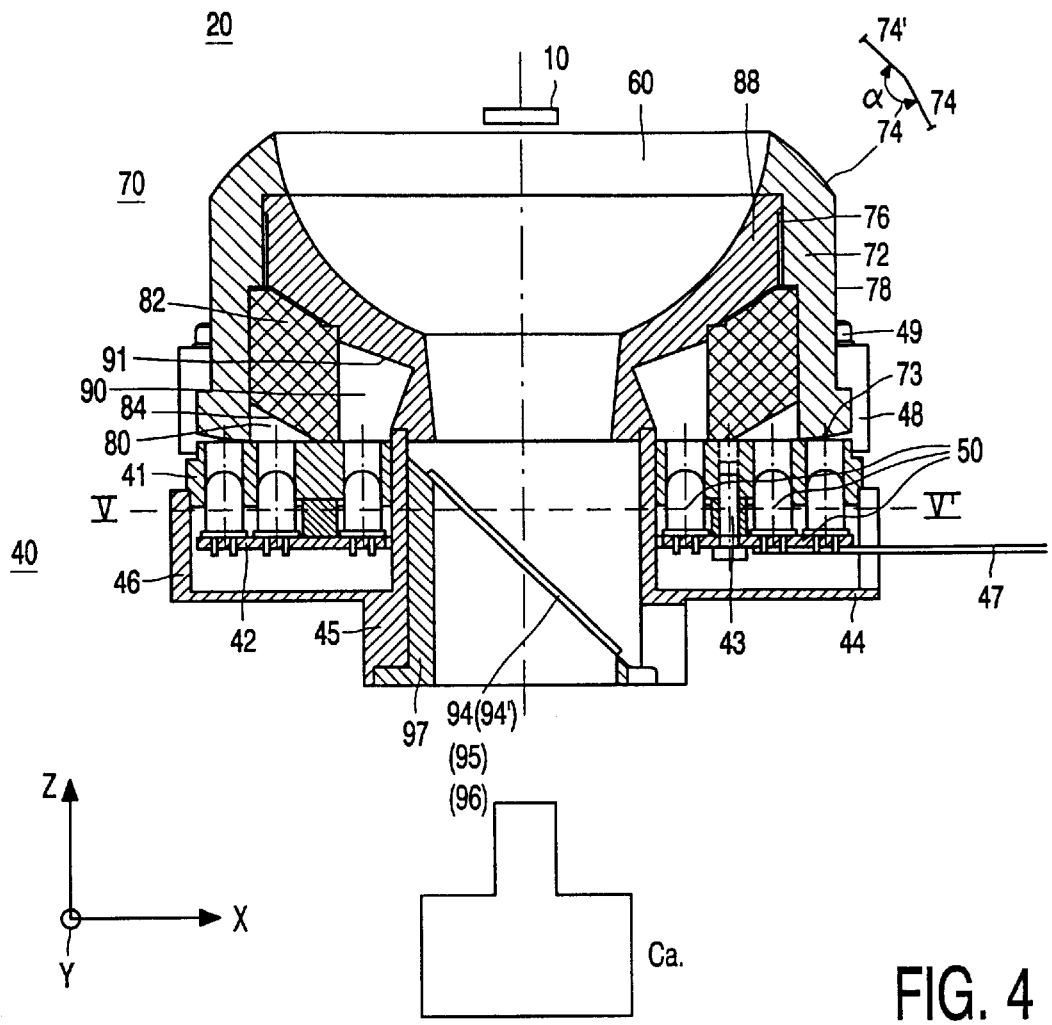
FIG. 4 shows an embodiment of the illumination module in accordance with the invention.

The present invention provides a compact, universal and programmable illumination module by means of which any one of the above-mentioned types of illumination can be realized either separately or in a combination of two or more of these types of illuminations. FIG. 4 shows an embodiment of this illumination module.

The module comprises a cylindrical base part 40 wherein the illumination rings are provided and an, also cylindrical, upper part 70 wherein radiation guides are provided. The base part 40 comprises a base plate 41. Below this plate, there is a plate 42 on which radiation-generating elements 50 are provided. The plate 42 is secured onto the base plate by means of screws 43. The radiation-generating elements are cut off from the surroundings by means of a cover 44 having an inner wall 45 and an outer wall 46. The radiation-generating elements 50 are distributed over a number of illumination rings. In the embodiment shown, there are three rings 62, 64 and 66.

Figure 5:
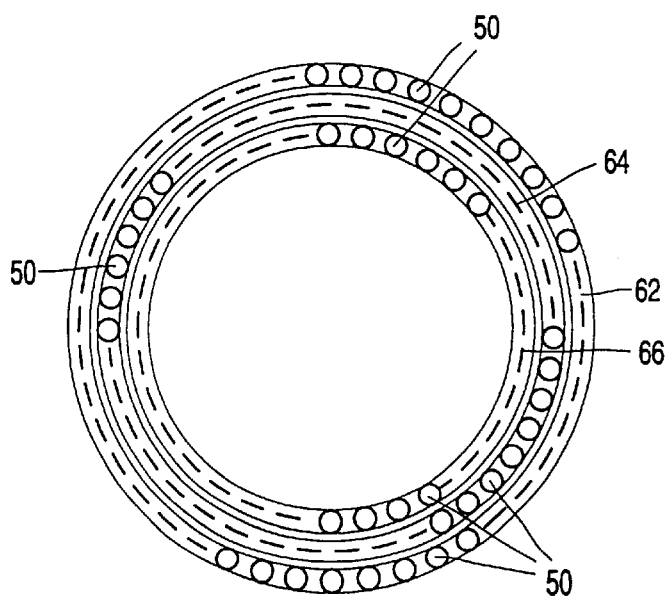
FIG. 5 is a plan view of the illumination rings of this module.

FIG. 5 is a sectional view in accordance with the plane V-V' of FIG. 4, and a plan view of the illumination rings 62, 64 and 66 with the radiation-generating elements 50.

The plate 46 is preferably embodied so as to be a printed circuit board. In this case, the plate comprises all connections and electric conductors for all radiation-generating elements 50. Reference numeral 47 indicates a power supply cable which can be connected to an electric supply source, not shown, which supplies all elements 50 with the necessary current.

The upper part 70 is secured onto the base part 40 by means of a clamping member 48 and screws 49. As the upper part is slid over a part of the inner wall 45 of the cover, this upper part, and the radiation guides present therein, are aligned with respect to the plate 42 and the radiation-generating elements 50. The number of radiation guides in the upper part 70 is equal to the number of illumination rings. In an X-Y plane, these radiation guides are ring-shaped in section. The entrance plane 73 of the outermost radiation guide 72 is situated above the illumination ring 62. This radiation guide continues as far as the upper side of the cap 70, where it has an oblique upper surface 74, and ensures that the radiation originating from the illumination ring 62 is incident on the component or the object 10 at angles of, for example, 70° to, for example, 88° with the normal to the component, i.e. the Z-axis. The radiation guide 72 is composed, for example, of a synthetic resin such as PC or PMMA, which is highly transparent to the radiation from the illumination ring 62. This radiation propagates either directly or via internal reflections at the inner wall 76 and the outer wall 78, and is reflected by the oblique upper surface 74 towards the component.

Preferably, the oblique upper surface consists of two parts 74' and 74" which enclose an obtuse angle α of at least 170° with each other. In this case, the beam passing through the radiation guide 72 is divided into two sub-beams whose main rays enclose an angle with each other such that they are superposed at the location of the object to be illuminated. If a radiation-generating element of the illumination ring 62 has, for example, a clock-shaped or Gaussian intensity distribution, so that the intensity in the center is greater than at the edges, then, viewed in the plane of the drawing of FIG. 4, the uppermost sub-beam has a greater intensity at the lower side than at the upper side, while the reverse applies to the lowermost sub-beam. By superposing the sub-beams, the intensity is averaged out and the two sub-beams jointly have a more uniform distribution.

The entrance plane 73 of the radiation guide is preferably arranged slightly obliquely so that the radiation originating from the illumination ring 62 is refracted and propagates in an optimal manner through the guide 72, whereafter it is incident on the oblique upper surface 74 at an optimum angle. Scattering particles may have been provided in the transparent material of the radiation guide 72, so that this guide itself also acts as a diffuser thereby rendering the radiation exiting from the guide more uniform. The diffuse radiation guide 72 ensures, in particular, that the individual, radiation-generating elements 50 of the illumination ring 62 are no longer visible in the illumination field not to the imaging optics and the camera.

The assembly of the illumination ring 62 and the radiation guide 72 is used if a "grazing" illumination of the component 10, or the object, must be realized, for example for making relief details in the surface of this object clearly visible.

Above the central illumination ring 64 there is a second radiation guide 80 which is formed by a space between the inner wall 76 of the outermost light guide 72 and the lower surface 84 of an element 82. The space 80 can be filled with air or a transparent material, for example a synthetic resin. The lower surface 84 is preferably obliquely positioned at a certain angle to ensure that the radiation from the illumination ring enters the element 82 at an optimum angle. This element 82 ensures that the radiation leaving the light guide obtains a homogeneous intensity distribution and is radiated within the desired angle interval. A diffuser element 88 is provided on the element 82. The element 88 makes sure that, in particular, the individual, radiation-generating elements of the illumination ring 64 are no longer visible in the illumination field nor to the imaging optics and the camera.

By means of the assembly: illumination ring 64, light guide 80 and element 82, the component can be illuminated with radiation the rays of which enclose angles of, for example, 40° to, for example, 72° with the Z-axis. This is a first type of dark-field illumination that can be generated by the illumination module.

A second type of dark-field illumination, the rays of which enclose angles of, for example, 20° to, for example, 40° with the Z-axis is generated by the assembly of the innermost illumination ring 66, the radiation guide 90 situated thereabove, and the part of the diffuser element 88 which is situated above the radiation guide 90. The upper surface 91 of the radiation guide 90 is arranged at a specific, oblique angle to make sure that the radiation from the illumination ring leaves the element at the desired angles. This radiation guide may be a space filled with air, or it may be formed by a transparent element of, for example, a synthetic resin.

Scattering particles may also be provided in this synthetic resin to render the radiation guide 90 diffuse to a certain degree.

The control circuit for the radiation-generating elements may be embodied so that the elements are switched on per illumination ring, and not simultaneously. In this, programmable, embodiment of the illumination module, one of the above-mentioned types of illumination can be chosen, i.e. grazing illumination, first type of background illumination and second type of background illumination, or a combination of two or more types of illumination can be chosen, so that the illumination can be optimally adapted to the desired object. The control circuit may additionally be embodied so that the intensity can be varied per illumination ring, so that even more illumination programs become possible. As a result, a better balance between the illumination fields of the different illumination rings can be obtained, which balance is adapted to the specific shape and reflection coefficients of the component and the details therein, which reflection coefficients may be different. If the illumination module is intended for an application wherein the bright-field illumination and the different types of dark-field illumination are employed simultaneously, the control circuit may be embodied so that all radiation-generating elements are switched on simultaneously. It is also possible to ensure that the different illumination rings have different intensities.

Dependent upon the application, the illumination module may also comprise two or more than three illumination rings and the associated radiation guides. Also in the case of more than three illumination rings, the outermost illumination ring is used to generate grazing illumination. In the case of more than three illumination rings, for example, the illumination field of the module can be enlarged. In this case, the illumination module may be constructed so that a plurality of illumination rings is present per radiation guide. It is alternatively possible that, also in the case of a plurality of illumination rings, an individual radiation guide is present for each illumination ring. As a result, the illumination can be further refined in that the number of different angle areas at which the object can be illuminated is increased.

The embodiment of the illumination module shown in FIG. 4 is specially intended for an observation device in a component placement machine. To preclude that a component 10 which prematurely has become detached from the suction pipette falls on the camera lens, which may retard the observation and placement process, a transparent plate 94, for example of glass, is provided at the lower side of the module at an angle of, for example, 45° with the Z-axis. This plate enables a component which has become detached prematurely to be laterally removed and caught, for example, in a receptacle which is not shown. The plate 94 is provided in a holder 97 which is secured on the inner wall 45 of the cover 44 and hence is fixed with respect to the base plate 41.

By embodying the plate 94 so as to be a filter, said plate can fulfill a second, optical function. The filter may be a spectral filter 95 which passes only radiation of a wavelength equal to that of the radiation emitted by the radiation-generating elements, and blocks ambient radiation. By virtue thereof, the contrast of the observed image of the component can be increased. The filter may alternatively be embodied so as to be a grey filter 96. By means of such a grey filter, the intensity of the illumination radiation originating from the component can be adapted to the sensitivity of the camera, so that the illumination module can be combined with different cameras. The grey filter also enables the intensity of the illumination radiation to be further increased to a value above that of the ambient light, so that the influence of the ambient light on the observation can be reduced.

Figure 6:
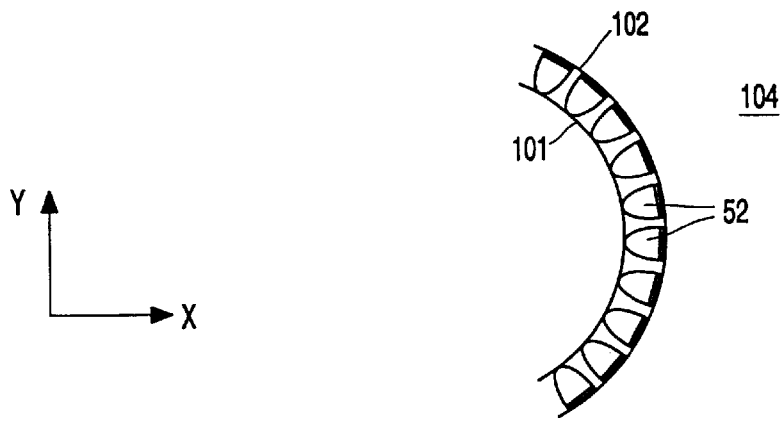
FIG. 6 is a plan view of a holder with additional, radiation-generating elements for an illumination module with bright-field illumination.

The illumination module shown in FIG. 4 can be extended to include a bright-field illumination. This requires the plate 94 to be embodied so as to be a beam splitter or semi-transparent plate 94', which reflects the bright-field radiation to the component 10 and allows the bright-field illumination radiation reflected by the component and said types of dark-field illumination radiation reflected by the component to pass to the camera. The bright-field illumination is generated by a number of radiation-generating elements 52 (FIG. 6) which are situated to the right of the beam splitter which is arranged so that the principal rays of the radiation beams emitted by these elements are incident on the beam splitter 94'. As regards the number of elements 52 and the positions thereof, there are various possibilities. To obtain maximum intensity for the bright-field illumination, while the illumination module remains compact, the elements 52 are preferably positioned in accordance with a circle segment, as is shown in FIG. 6. This Figure shows the collection of elements 52 in a sectional view in accordance with an XY plane. Reference numerals 101 and 102 indicate the inner wall and the outer wall, respectively, of a holder 104 (FIG. 6) wherein the elements 52 are provided. In this holder, one or more layers or rows of elements 52 may be provided, dependent upon the desired intensity of the foreground illumination and the space available. The holder 104 may be shaped in the form of a ring segment wherein the elements 52 are arranged in accordance with a circle segment which harmonizes with the shape of the module in accordance with FIG. 4. The holder 104 may alternatively be rectangular, so that the elements 52 can be provided more readily. The holder 104 is preferably filled with a diffuse material, for example a transparent synthetic resin wherein scattering particles are provided, so that the radiation leaving this holder already exhibits a certain degree of homogeneity.

Figure 7:
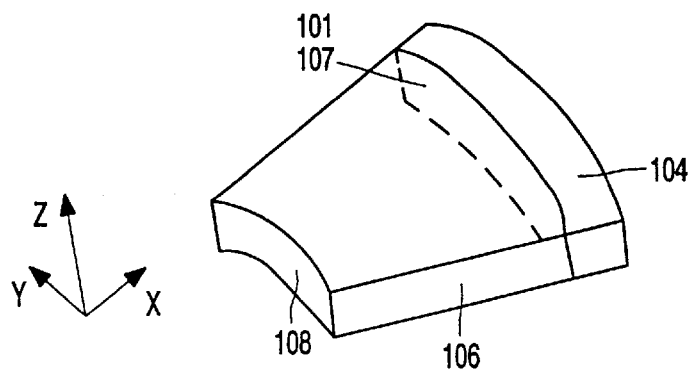
FIG. 7 is a perspective view of this holder combined with a first radiation guide.

As shown in FIG. 7, a radiation guide 106 may be provided so as to engage the holder 104. This Figure is a perspective view of the radiation guide 106 together with the holder 104. This radiation guide ensures that the radiation of the elements is focused and, to a certain extent, rendered homogeneous. If the holder 104 is shaped so as to be bent, the entrance surface 107 of the radiation guide 106 preferably has the same curvature as the inner wall of the holder 104. The exit surface 108 of the radiation guide 106 preferably has a smaller radius of curvature than the entrance surface 107, so that this guide has a focusing effect in the XY plane.

Figure 8:
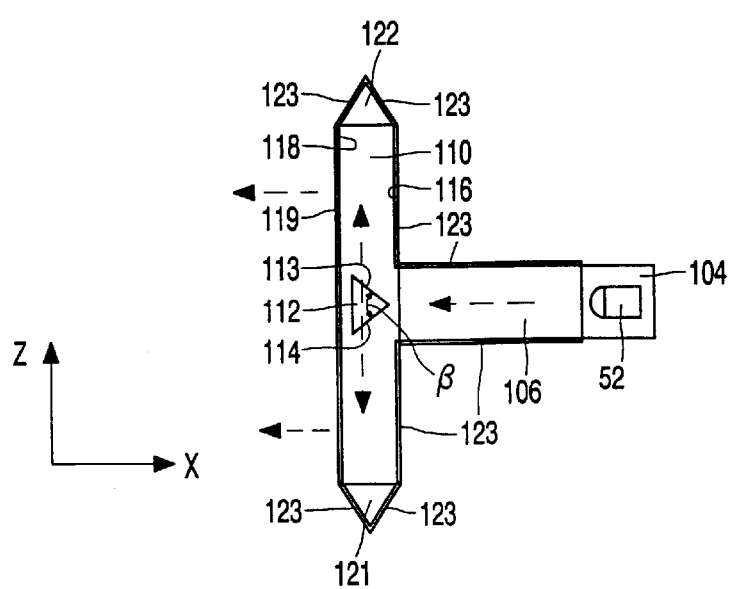
FIG. 8 is a cross-sectional view of a unit consisting of this combination and a second radiation guide.

To obtain a satisfactory, uniform illumination of the beam splitter 94' and hence of the component 10, a further radiation guide 110 is provided so as to engage the radiation guide 106, as shown in FIG. 8. This Figure shows the radiation guide 110 and the radiation guide 106 in vertical section, i.e. a section in accordance with a ZX plane. To distribute the radiation exiting the radiation guide 106 over the radiation guide 110, a reflecting element 112 is present which is arranged symmetrically with respect to the exit surface of the radiation guide 106. In the embodiment shown in FIG. 8, this element is formed by two surfaces 113 and 114 which enclose such an angle β that the major part of the radiation incident thereon is reflected and a small part is passed to the exit plane 118 of the radiation guide 110. The radiation reflected upwards by the surface 113 is subject, in the radiation guide 110, to a number of internal reflections at the surfaces 116 and 118 of the radiation guide 110 until said radiation is incident on the exit surface 118 at such an angle that the radiation is passed by this surface to the beam splitter 94'. The same applies to the radiation which is reflected downwards by the surface 114.

The radiation guides 106 and 110 are composed of a transparent material, for example a transparent synthetic resin such as PC or PMMA. A diffuser layer 119 may be additionally applied to the exit surface 118 of the radiation guide 110, so that the bright-field illumination is very homogeneous. To preclude radiation from exiting at the lower side and the upper side of the radiation guide 110, these sides may be embodied so as to be reflecting prisms 121 and 122. To ensure good reflection within the radiation guides, a reflecting layer 123 may be applied to the surface 116, and to the surfaces of the prisms 121 and 122 of the radiation guide 110, and to the surfaces of the radiation guide 106, as shown in FIG. 8.

Figure 9:
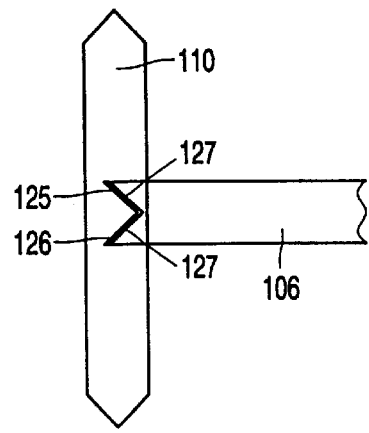
FIG. 9 shows an alternative, preferred, unit of this type.

FIG. 9 shows an alternative, preferred embodiment wherein the reflecting surfaces 113 and 114 in the radiation guide 110 are substituted with reflecting surfaces 125 and 126 in the radiation guide 106. The provision of these surfaces at the head end of the radiation guide 106 can be carried out more readily than the provision of the surfaces 113 and 114 in the center of the radiation guide 110 so as to be properly aligned with respect to the radiation guide 106. Moreover, in this manner the homogeneity of the material of the radiation guide 110 is better ensured. The radiation guide 106 must project so far into the radiation guide 110 that surfaces 125 and 126 are situated on the left-hand side of the surface 116 of the radiation guide 110. To preclude undesirable reflections, the material of the radiation guide 106 should preferably be the same as that of the radiation guide 110. As the embodiments of FIG. 8 and FIG. 9 are the same for the rest, FIG. 9, unlike FIG. 8, does not show all details.

The surfaces 125 and 126 in the embodiment of FIG. 9, as well as the surfaces 113 and 114 in FIG. 8, may be additionally provided with a reflecting layer 127, for example in the form of a white lacquer layer, to obtain the desired reflection.

Figure 10:
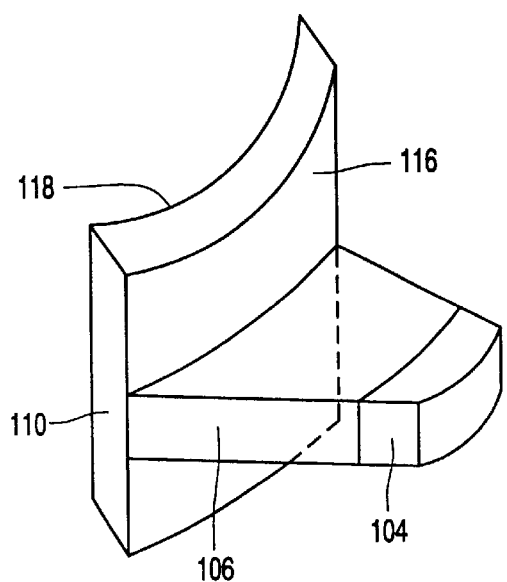
FIG. 10 is a perspective view of these units.

Preferably, the radiation guide 110 is shaped so as to be in the form of a bent plate, as shown in FIG. 10. This Figure shows the assembly of the light guides 106 and 110 and the holder in a perspective view. The curvature of the surface 116 can be adapted to that of the inner wall of the innermost illumination ring 66, so that the upper part of the radiation guide 110 can be introduced into the space between this inner wall, causing this part to engage the inner wall 45 or be situated at the location of the inner wall 45 (FIG. 4). As a result, a compact construction is also obtained for the illumination module to which a bright-field illumination has been added.

The dimension in the Z-direction of the exit surface 118 may be equal to that of the beam splitter 94', so that, in this direction, the entire surface of the beam splitter is irradiated. As a result, the radiation from the foreground illumination fills the space between this exit surface and the inner wall of the illumination ring 66 to the extent possible. In addition, the curvature of the exit surface 118 can be chosen to be such that, also in the Y-direction, substantially the entire surface of the beam splitter is irradiated and said space is filled to the extent possible. The angles which the rays of the foreground illumination include with the Z-axis at the location of the component range, for example, from 0° to 16°.

The radiation-generating elements 50 and 52 are preferably light-emitting diodes, also referred to as LEDs. At present, various types of LEDs are available having different formats and producing radiation beams having different aperture angles and intensities as well as different colors, thus enabling the proper LEDs to be chosen for a specific application. As regards the illumination module in question, the aperture angle lies in the range from 20° to 40° and is preferably 30°. Under special conditions, for example if switching does not have to take place rapidly, instead of LEDs, use can be made of luminescent diodes, which are cold radiation sources, for the radiation-generating elements. It is alternatively possible to use diode lasers for the radiation-generating elements. Diode lasers issue a relatively narrow beam with a small aperture angle and a large intensity, and the radiation thereof can be accurately directed.

Figure 11:
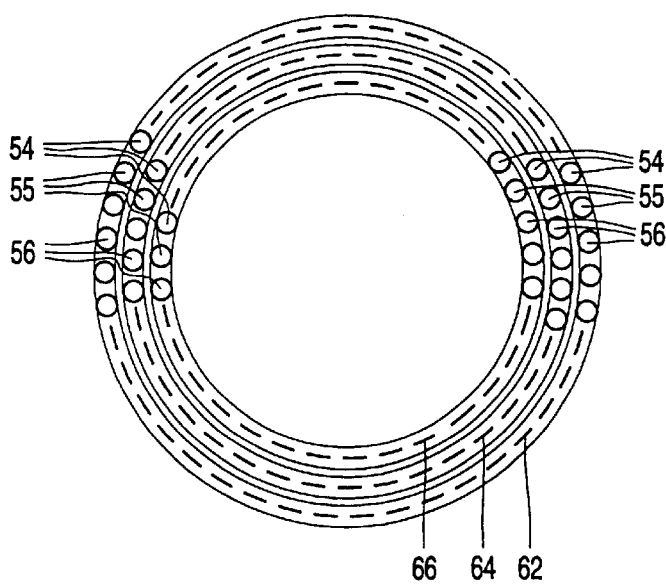
FIG. 11 is a plan view of illumination rings with LEDs of different colors.

Hitherto it has been assumed that all radiation-generating elements emit light of a same color and that all elements 50 of one illumination ring or all elements 52 for the bright-field illumination are switched on simultaneously. In the field of application of the illumination module there are components whose color is such that they cannot be readily observed when the radiation is of the color to which the monochrome camera is most sensitive. For example, when green light is used, it is difficult to recognize a yellow component. Also a brown object against a grey background, or a yellow object against a green background are difficult to observe. In order to be able to properly observe different types of components which may have different colors and may be placed against backgrounds of different colors, LEDs emitting different colors, such as red, green and blue LEDs, can be provided in one and the same illumination ring. This is shown in FIG. 11, which Figure corresponds to FIG. 5 with the exception that the LEDs 50 are replaced by red LEDs 54, green LEDs 55 and blue LEDs 56, which LEDs alternate with each other along the arc of a circle. The switching circuit is embodied in such a manner that the LEDs of one color are switched on simultaneously, while it is also possible to simultaneously switch on the LEDs of only one color or the LEDs of two colors or the LEDs of three colors. Since the LEDs of one color are positioned at a greater distance from each other, the overall radiation of these LEDs is, in principle, less homogeneous. However, in the illumination module in accordance with the invention this does not constitute a drawback because the radiation guides 72, 82 and 84 present therein provide for sufficient homogenization of the radiation originating from the LEDs of a single color. When LEDs of different colors are simultaneously used, said radiation guides additionally ensure that the different colors are properly mixed.

The combination of red, green and blue LEDs enables any illumination color to be obtained, i.e. any illumination color that is optimally adapted to the circumstances. Instead of LEDs of three different colors, it is alternatively possible to use, for example, LEDs of only two different colors. Also the collection of LEDs 52, shown in FIG. 6, for the bright-field illumination may be composed of LEDs of two or more colors. It is also possible that one or more illumination rings comprise only LEDs of the same color, which color is different for the different illumination rings.

The illumination module can suitably be used to optimally illuminate various kinds of electronic components. Mention has already been made of a SMD component, which can be considered to be a block with projecting connection pins for securing and contacting the component to the exterior. Another type of component is the so-called Ball Grid Array (BGA); a component in the form of a block on a surface of which a number of balls are provided for making contact with the exterior, and the positions of which should be accurately determined. Yet another kind of component is the so-called flip-chip; a component which is similar to the BGA but comprises smaller balls. Also smooth, reflecting components can be properly observed by means of an observation device provided with the illumination module described herein.

The invention has been described by means of illuminating and observing electronic components in a component-placement machine, however, the field of application of the invention is by no means limited thereto. The illumination module in accordance with the invention can be used in various observation devices (vision modules) for many applications, such as in measuring machines for measuring dimensions and surface gradients of objects, or inspection machines for inspecting surface irregularities, such as roughness and luster, of objects.

The illumination module is unique in that it combines the following advantages:
   a number of illumination principles are integrated in a module so as to be in balance, as a result of which this module is universally applicable;
   the module is compact;
   the module enables a very homogeneous illumination, with a variation below 2%, to be realized;
   as the module is composed of sub-modules, it can be readily extended to include additional illumination rings to enlarge the illumination field, and, if desired, additional radiation guides;
   by using a flat printed circuit board as the holder for the radiation-generating elements, and by other constructive details, the module can be readily manufactured and is also suitable for mass-production.

What is claimed is:

1. An illumination module for illuminating an object to be examined, which module comprises an exit window for radiation generated in the module, a module axis which extends perpendicularly to the central part of the exit window, and a number of radiation-generating elements which are arranged in at least two illumination rings, which illumination rings have a midpoint, which is situated on the module axis, and are individually switchable, the radiations of the different illumination rings passing through the exit window at different angles with respect to the module axis, characterized in that all the radiation-generating elements are provided on a flat plate which extends parallel to the central part of the exit window, and the principal rays of all radiation beams emitted by the radiation-generating elements extend parallel to the module axis.

2. An illumination module as claimed in claim 1, characterized in that opposite each illumination ring there is provided a radiation guide which, in a plane at right angles to the module axis, is ring-shaped in section, the entrance plane of said radiation guide being situated opposite the associated illumination ring, and the shape of the light guide's exit plane situated opposite the entrance plane being adapted to the desired direction of the radiation to be supplied by the associated illumination ring.

3. An illumination module as claimed in claim 2, characterized in that the radiation guides, possibly with the exception of the innermost radiation guide, are filled with a transparent synthetic resin.

4. An illumination module as claimed in claim 3, characterized in that the synthetic resin is polycarbonate or polymethyl methacrylate.

5. An illumination module as claimed in claim 3, characterized in that the synthetic resin comprises scattering particles.

6. An illumination module as claimed in claim 1, characterized in that the outermost radiation guide has a reflective surface for reflecting radiation towards the exit plane of this radiation guide, which reflective surface consists of two parts which enclose an obtuse angle with each other.

7. An illumination module as claimed in claim 1, characterized in that it comprises three illumination rings.

8. An illumination module as claimed in claim 1, characterized in that the radiation-generating elements are formed by LEDs.

9. An illumination module as claimed in claim 8, characterized in that at least one of the illumination rings comprises at least two types of LEDs, which emit radiation of different wavelengths, and LEDs of the first type alternating with LEDs of the other type(s) in said illumination ring.

10. An illumination module as claimed in claim 1, characterized in that, within the central illumination ring, a transparent plate is provided which encloses an acute angle with the module axis.

11. An illumination module as claimed in claim 10, characterized in that an optical filter is provided on the plate.

12. An illumination module as claimed in claim 11, characterized in that the optical filter is a color filter.

13. An illumination module as claimed in claim 11, characterized in that the optical filter is a grey filter.

14. An illumination module as claimed in claim 1, characterized in that, within the central illumination ring, a semi-transparent plate is provided at an angle of, in principle, 45° with respect to the module axis, and in that an additional radiation source is provided which is arranged such that radiation from this source is incident on the semi-transparent plate and reflected thereby towards the exit window of the illumination module.

15. An illumination module as claimed in claim 14, characterized in that the additional radiation source is formed by a number of additional radiation-generating elements arranged in at least one row, in combination with a first radiation-guiding plate the entrance face of which is directed towards the row of additional radiation-generating elements, and the exit face of which is directed towards the semi-transparent plate.

16. An illumination module as claimed in claim 15, characterized in that the additional radiation-generating elements are arranged in at least one circle segment at one side of the transparent plate.

17. An illumination module as claimed in claim 15, characterized in that a second radiation-guiding plate is arranged against the exit face of the first radiation-guiding plate at an angle of, in principle, 90°, and in that two reflecting surfaces are situated at the location of the transition from the first radiation-guiding plate to the second radiation-guiding plate, so as to reflect, partly and in two opposite directions in the second radiation-guiding plate, two halves of radiation exiting from the first radiation-guiding plate.

18. An illumination module as claimed in claim 17, characterized in that the two reflecting surfaces are provided in the second radiation-guiding plate.

19. An illumination module as claimed in claim 17, characterized in that the two reflecting surfaces are part of the first radiation-guiding plate.

20. An illumination module as claimed in claim 17, characterized in that the second radiation-guiding plate takes the form of a cylinder segment whose cylinder axis extends parallel to the module axis.

21. An illumination module as claimed in claim 15, characterized in that the additional, radiation-generating elements are formed by at least two kinds of radiation generating elements which emit radiation of different wavelengths, and in that, in a row, elements of the first kind alternate with elements of the other kind(s).

22. An observation device for observing an object and provided with an illumination system for illuminating the object, and a camera for receiving an image of the object, characterized in that the illumination system is an illumination module as claimed in claim 1.

23. A component-placement machine for placing electronic components on a support, which machine is provided with:

a frame;

at least one robot;

a transport system for transporting supports;

a placement head for each robot for placing components on a support, which placement head is secured to an arm of the robot, and component-positioning means for each robot for positioning a component which is held by the placement head associated with the robot, characterized in that the component-positioning means comprise an observation device as claimed in claim 22.

* * * * *